US00PP17130P2

(12) United States Plant Patent
Korlipara

(10) Patent No.: US PP17,130 P2
(45) Date of Patent: Oct. 3, 2006

(54) ***VERBASCUM* PLANT NAMED 'BLUSHING BRIDE'**

(50) Latin Name: ***Verbascum* hybrid**
Varietal Denomination: Blushing Bride

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 3 days.

(21) Appl. No.: 11/153,741

(22) Filed: Jun. 14, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct *Verbascum* plant characterized by numerous soft lavender colored flowers on numerous short, upright flowering stems, a compact habit, and excellent vigor.

1 Drawing Sheet

Botanical classification: *Verbascum* hybrid ((*V. phoeniceum*×*dumulosum*)×*V. phoeniceum*).

Variety denomination: 'Blushing Bride'.

Cross reference to: *Verbascum* 'Plum Smokey' (U.S. Plant Pat. No. 16,156) and *Verbascum* 'Sugar Plum' (U.S. Plant Pat. No. 16,224), *Verbascum* 'Lavender Lass' (U.S. Plant Patent Application Ser. No. 11/045,227).

The present invention relates to a new and distinct cultivar of *Verbascum* hybrid, and given the cultivar name 'Blushing Bride'. *Verbascum* is in the family Scrophulariacae.

This new cultivar originated from a cross between *Verbascum* 'Jackie' (unpatented) as the seed parent and an unnamed selection of *Verbascum phoeniceum* as the pollen parent. *Verbascum* 'Jackie' is an unpatented plant and a cross between *Verbascum phoeniceum* and *Verbascum dumulosum*.

The new *Verbascum* hybrid is unique in its soft lavender flower color combined with its *Verbascum* 'Jackie'-like compact habit and short, multiple flowering stems.

This plant is characterized by the following:

1. Large soft lavender flowers.
2. Numerous upright, branching flowering stems.
3. Compact habit.
4. Short flowering stems.
5. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the whole plant of *Verbascum* 'Blushing Bride' grown in the ground in the trial field in bloom in late spring.

DETAILED PLANT DESCRIPTION

The following is a detailed description of the new *Verbascum* selection based on observations of one-year-old specimens in the ground in full sun under typical outdoor conditions in the field in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Type.*—Herbaceous perennial.
*Form.*—Clumping basal rosette.
*Hardiness.*—U.S.D.A. Hardiness Zones 5–9.
*Size.*—13 cm tall and 35 cm wide, not including inflorescence.
*Vigor.*—Excellent.
*Roots.*—With one main tap root, and many fibrous lateral branches, White 155A.
*Stem.*—Much congested, 1 cm deep and wide with no space between internodes.

Leaf:

*Type.*—Simple, evergreen in Canby, Oreg.
*Arrangement.*—Basal, with 30 to 35 leaves.
*Shape.*—Ovate to oblong.
*Blade size.*—Grows to 17 cm long and 7.5 cm wide.
*Venation.*—Pinnate.
*Margins.*—Irregularly crenate overall and toothed near base.
*Apex.*—Acute.
*Base.*—Cuneate.
*Surface texture.*—Stellate.
*Petiole description.*—2.5 cm long, grows to 8 mm wide, stellate hairs, Yellow Green 147C where shaded, Greyed Purple 185A in sun.
*Leaf color.*—Topside — Deep green. Green 147A with reddish main vein, Greyed Purple 185A. Bottom side —Yellow Green 147B.

Inflorescence:

*Type.*—Panicle.
*Total panicle size.*—12 cm wide and 35 cm high (where flowers are).

*Number of panicles per plant.*—8 in first flush.

*Cauline leaves.*—3 to 5 in number, grow to 3.5 cm long and 2.5 cm wide, with an acute tip and cuneate base, margins irregularly crenate overall and toothed near base, upper surface is Green 137A with a lighter main vein, Yellow Green 145D and the lower surface is between Yellow Green 147B and Green 137C.

*Flower number.*—Count of 300 flowers on one panicle.

*Peduncle description.*—40 cm tall, 8 mm wide near base, stellate and glandular hairs, Yellow Green 148A to C.

*Pedicel description.*—8 to 10 mm long, glandular hairs, Yellow Green 148A.

*Bloom time.*—May to August in Canby, Oreg.

Flower bud:

*Size.*—11 cm wide and 7 mm deep.

*Description.*—Pentagonal cushion.

*Surface.*—Glandular hairs.

*Color.*—Greyed Purple 187A to Purple 79D.

Flower:

*Type.*—Perfect, complete, irregular.

*Shape.*—Rotate, irregular, short tublar.

*Size.*—3.5 cm wide and 1 cm deep including stamens.

*Color.*—Dull pink, Between Greyed Purple 186C and Violet 85D with a darker center Violet 85B.

*Corolla description.*—5 lobes, broadly obovate, margin entire, top obtuse, base cuneate, 3.5 cm wide and 5 mm deep, back side with glandular hairs.

*Calyx description.*—6 mm wide and 6 mm deep, campanulate with 5 lobes, each lobe lanceolate with entire margins and an acuminate tip, glandular hairs on outside, Green 138A on both surfaces.

*Stamen description.*—5 in number, filaments 7 mm long, Yellow 11A at base and heavily bearded Purple 79B topped with White 155A on upper three stamens, anthers kidney shaped, 2 mm long, Greyed Purple 185A, pollen Orange 24A.

*Pistil description.*—Style is 7 mm long, Greyed Purple 183A, stigma is blunt, stigma and ovary are Green 138D.

*Fragrance.*—None.

Fertility: Sterile, no fruit or seed produced.

Disease and pests: *Verbascum* are susceptible to fungal leaf spots and root rots. They need good drainage. Caterpillars may be a problem.

COMPARISONS

This new cultivar is very similar in growth habit and flowering habit to *Verbascum* 'Jackie' (unpatented). The greatest difference is the flower color. *V.* 'Jackie' is described as having copper colored buds, which open to pale peach colored flowers and lavender stamens. The new cultivar has dull purple buds that open to soft lavender flowers. *Verbascum* 'Blushing Bride' the same good qualities of numerous flowering stems, short flowering stems, and compact habit of *Verbascum* 'Jackie'.

Compared to its pollen parent, *Verbascum phoeniceum*, the new cultivar has a longer bloom time, more flowering stems, soft lavender rather than pink flowers, and larger flowers.

Compared to *Verbascum* 'Plum Smokey' (U.S. Plant Pat. No. 16,156), the new cultivar is taller, and the flowers are smaller and a soft lavender rather than a plum purple color.

Compared to *Verbascum* 'Sugar Plum' (U.S. Plant Pat. No. 16,224), the new cultivar has smaller flowers that are a soft lavender rather than purple color.

Compared to *Verbascum* 'Lavender Lass' (U.S. Plant Patent Application Ser. No. 11/045,227), the new cultivar has smaller flowers of a muted lavender rather than a clear lavender color and shorter flowering stems.

I claim:

1. A new and distinct *Verbascum* plant characterized by numerous soft lavender colored flowers on numerous short, upright flowering stems, a compact habit, and excellent vigor.

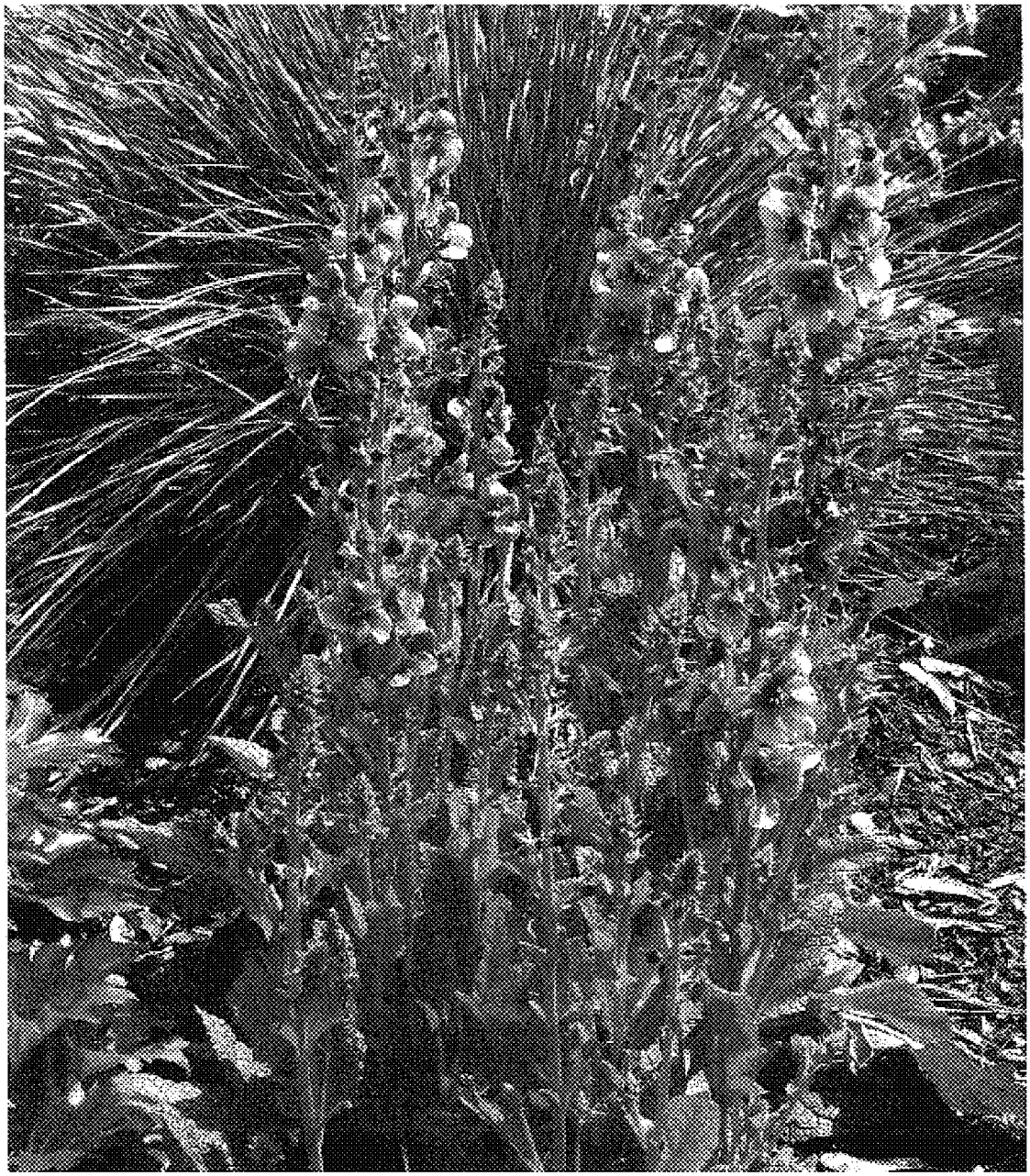

* * * * *